US006447729B1

(12) United States Patent
Tuunanen

(10) Patent No.: US 6,447,729 B1
(45) Date of Patent: Sep. 10, 2002

(54) METHOD AND MEANS FOR MAGNETIC PARTICLE SPECIFIC BINDING ASSAY

(75) Inventor: Jukka Tuunanen, Helsinki (FI)

(73) Assignee: Labsystems Oy, Helsinki (FI)

(*) Notice: Subject to any disclaimer, the term of this patent is extended or adjusted under 35 U.S.C. 154(b) by 0 days.

(21) Appl. No.: 09/479,615

(22) Filed: Jan. 7, 2000

Related U.S. Application Data

(63) Continuation of application No. 08/920,094, filed on Aug. 26, 1997, now Pat. No. 6,040,192, which is a continuation of application No. 08/495,514, filed on Aug. 28, 1995, now abandoned, which is a continuation-in-part of application No. PCT/FI94/00048, filed on Feb. 1, 1994.

(30) Foreign Application Priority Data

Feb. 1, 1993 (FI) .................................... 930440
Jun. 21, 1993 (FI) .................................... 932866

(51) Int. Cl.$^7$ ............................................. G01N 33/553
(52) U.S. Cl. ..................... 422/101; 435/287.3; 436/526
(58) Field of Search ................... 436/526, 806, 436/808, 177; 422/101, 65; 210/222, 695; 209/212–215, 217, 225; 435/287.1, 287.2, 287.3, 287.9

(56) References Cited

U.S. PATENT DOCUMENTS

| | | |
|---|---|---|
| 2,471,764 A | 5/1949 | Miller et al. |
| 2,683,618 A | 7/1954 | Long |
| 2,970,002 A | 1/1961 | Laviano |
| 3,904,482 A | 9/1975 | Mehl |
| 3,970,518 A | 7/1976 | Giaever |
| 3,985,649 A | 10/1976 | Eddelman |
| 4,018,886 A | 4/1977 | Giaever |
| 4,115,535 A | 9/1978 | Giaever |
| 4,197,287 A | 4/1980 | Piasio et al. |
| 4,200,613 A | 4/1980 | Alfrey et al. |

(List continued on next page.)

FOREIGN PATENT DOCUMENTS

| | | |
|---|---|---|
| DE | 2824742 A1 | 2/1979 |
| EP | 0 027 008 A1 | 4/1981 |
| EP | 0186001 | 7/1986 |
| EP | 0042755 A3 | 8/1988 |
| EP | 0317286 | 5/1989 |
| EP | 0351857 | 1/1990 |
| EP | 0358948 | 3/1990 |
| EP | 0479448 | 4/1992 |
| EP | 0522322 | 1/1993 |
| GB | 1414479 | 11/1975 |
| GB | 2147698 | * 5/1985 |
| JP | 58-5656 | 1/1983 |
| JP | 58-5657 | 1/1983 |
| JP | 58-5658 | 1/1983 |
| JP | 63-5263 | 1/1988 |
| JP | 63-5265 | 1/1988 |
| JP | 63-5266 | 1/1988 |
| WO | WO 8606493 | 11/1986 |
| WO | 87/05536 | * 9/1987 |
| WO | WO 9418564 | 8/1994 |

(List continued on next page.)

OTHER PUBLICATIONS

"AlNiCo Rod Magnets", *IBS Magnet*, Ing. K.–H. Scroeter, Kurfürstenstrasse 92, 12105 Berlin, Germany, p. 15.

*Primary Examiner*—Jan Ludlow
(74) *Attorney, Agent, or Firm*—Fish & Richardson P.C.

(57) ABSTRACT

An apparatus for separating magnetic particles from a solution includes a vessel with a smaller diameter lower portion and larger diameter upper portion, a magnetic remover and a positioner for the magnetic remover. The transition between the small and large diameter portions of the vessel facilitates separation of droplets from the magnetic remover as it is removed from the vessel, while still retaining magnetic particles.

11 Claims, 4 Drawing Sheets

U.S. PATENT DOCUMENTS

Figure 2B:
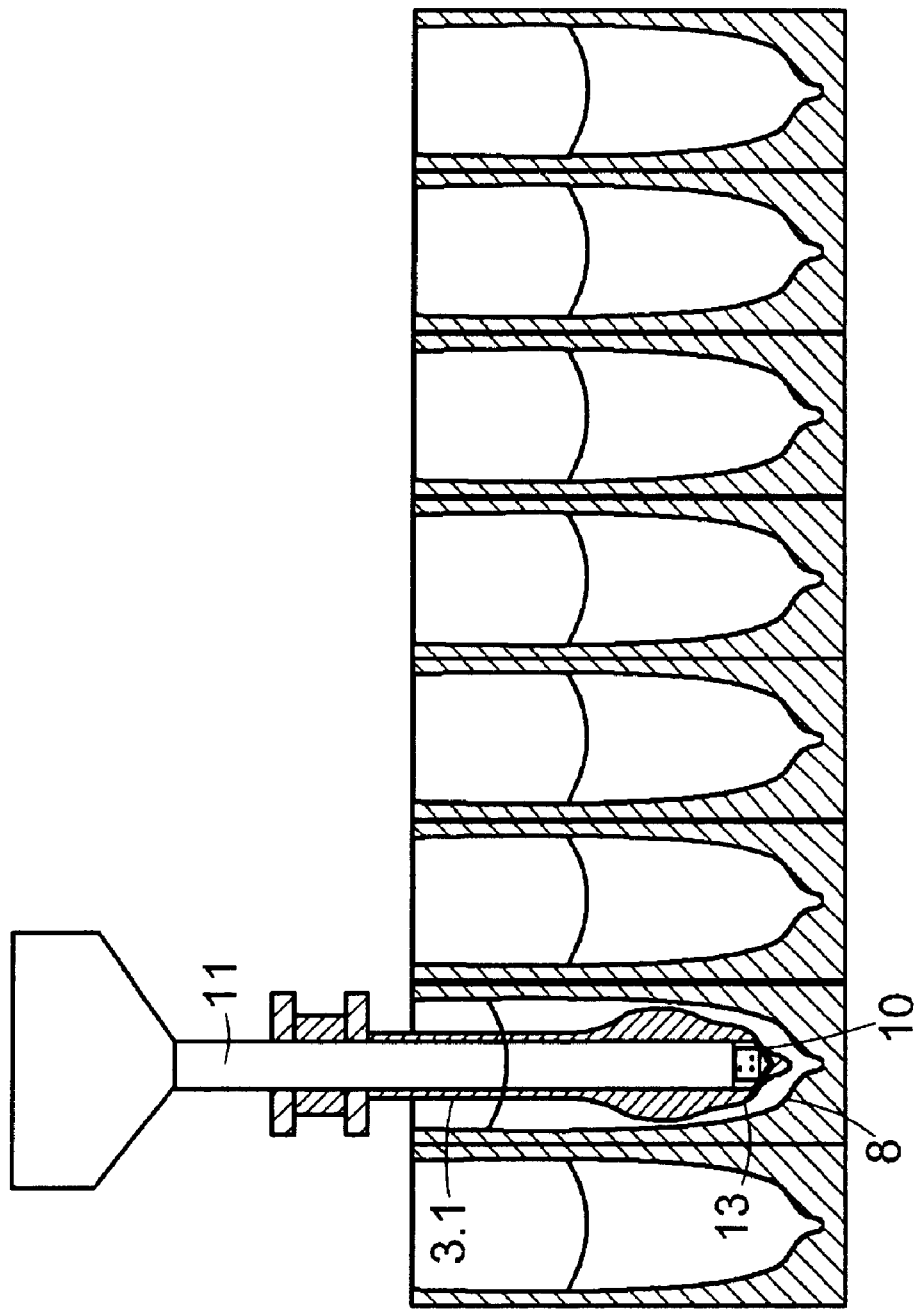

| | | | |
|---|---|---|---|
| 4,225,575 A | | 9/1980 | Piasio et al. |
| 4,261,815 A | | 4/1981 | Kelland ...................... 209/213 |
| 4,272,510 A | * | 6/1981 | Smith et al. |
| 4,438,068 A | | 3/1984 | Forrest |
| 4,495,151 A | | 1/1985 | Ohyama et al. |
| 4,649,116 A | | 3/1987 | Daty et al. |
| 4,681,742 A | * | 7/1987 | Johnson et al. |
| 4,731,337 A | | 3/1988 | Luotola et al. |
| 4,751,053 A | | 6/1988 | Dodin et al. |
| 4,891,321 A | | 1/1990 | Hubscher |
| 4,895,650 A | | 1/1990 | Wang |
| 5,066,390 A | | 11/1991 | Rhodes et al. ............... 209/217 |
| 5,167,926 A | | 12/1992 | Kimura et al. |
| 5,200,084 A | | 4/1993 | Liberti et al. |
| 5,206,034 A | | 4/1993 | Yamazaki |
| 5,316,151 A | | 5/1994 | Thompson ............... 209/223.1 |
| 5,318,914 A | | 6/1994 | Matte et al. |
| 5,340,749 A | * | 8/1994 | Fujiwara et al. |
| 5,466,574 A | | 11/1995 | Liberti et al. |
| 5,474,742 A | | 12/1995 | Tuuminen |
| 5,647,994 A | | 7/1997 | Tuunanen et al. |
| 5,942,124 A | | 8/1999 | Tuunanen |
| 6,020,211 A | | 2/2000 | Tuunanen |
| 6,040,192 A | | 3/2000 | Tuunanen |
| 6,065,605 A | | 5/2000 | Korpela et al. |
| 6,197,597 B1 | | 3/2001 | Tuunanen ................... 436/518 |
| 6,207,463 B1 | | 3/2001 | Tuunanen ................... 436/526 |

FOREIGN PATENT DOCUMENTS

| | | |
|---|---|---|
| WO | WO 9418565 | 8/1994 |
| WO | WO 9500247 | 1/1995 |
| WO | WO 9612958 | 5/1996 |
| WO | WO 9612959 | 5/1996 |
| WO | WO 9612960 | 5/1996 |
| WO | WO 9612961 | 5/1996 |

* cited by examiner

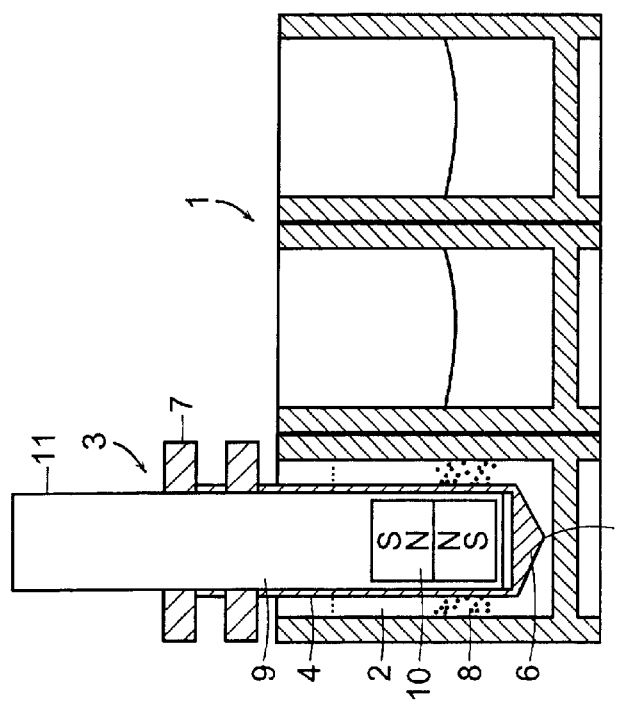
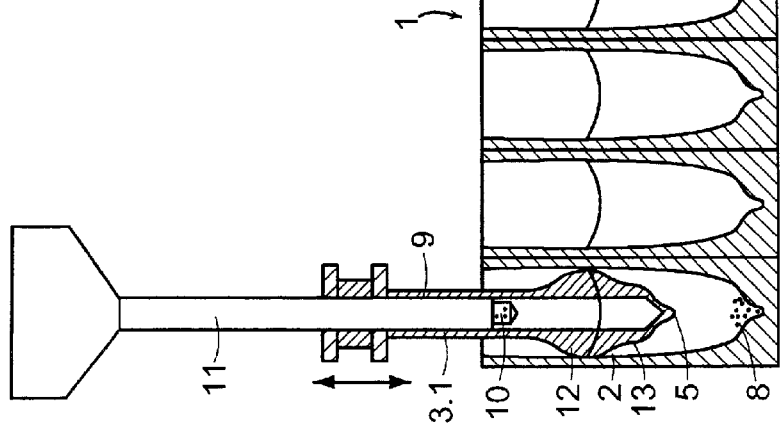
FIG. 1
FIG. 2A

METHOD AND MEANS FOR MAGNETIC PARTICLE SPECIFIC BINDING ASSAY

This application is a continuation of U.S. application Ser. No. 08/920,094, filed Aug. 26, 1997, now U.S. Pat. No. 6,040,192, which is a continuation of U.S. application Ser. No. 08/495,514, filed Aug. 28, 1995, now abandoned, which is a continuation of PCT/FI94/00048, filed Feb. 1, 1994.

TECHNICAL FIELD

The invention concerns a determination method and equipment as well as an adapter for use in these. The invention is especially applicable to automatic immunodetermination systems.

TECHNICAL BACKGROUND

Solid-phase immunodetermination is usually performed in one vessel so that the analyte to be determined and possibly contained in the sample is first allowed to react with a separating reagent bound in a solid phase, whereupon the other steps required in the determination are performed in the same vessel. The troublesome thing here is that much dosing and removing of liquids must be performed. When several different determinations are done, a large stock of different reagents is also needed.

A system is also known wherein the solution to be used in each determination step is placed in advance in its own vessel. The solid phase is formed by the inside surface of a disposable pipette jet. In each step the pipette jet is brought into the respective vessel, the solution is drawn into the jet and a reaction is allowed to take place, whereafter the jet is emptied and moved into the next vessel. During the step the solution is moved back and forth in the jet. The equipment has several suction cylinders with pumps so that several determinations can be performed in parallel. No exact dosing devices are required in this equipment. Nor are any reagent containers required in the equipment. However, the drawback is that through a vapour phase samples are in connection with the cylinders of the equipment which can not, however, be washed automatically. This can cause a risk of contamination. Liquid will also remain in the pipette jet and will move along to the following step. In addition, piston pumps wear easily and unpredictably, for which reason their condition must be checked often. Another problem is the sealing of the pipette jet to the suction cylinder. All things considered, much trouble can occur in this device. Besides, there is only limited solid-phase surface area available on the inner surface of the pipette jet.

DESCRIPTION OF THE INVENTION

A method of determination as defined in claim 1 has now been invented. Advantageous applications of the same are presented in the other claims.

As used herein, a separating reagent means such a substance which reacts with the analyte to be determined and binds it in a solid phase. In immunodeterminations the separating reagent is usually an antigen or an antibody. A medium here generally means a solution, such as a reaction solution or a washing fluid, to be used in some determination step.

The outer surface of solid particles separate from the reaction vessel is used as the solid phase in the method and the determination steps are carried out in two or several vessels. The particles are moved from one vessel to another using a special remover. The particles are kept in the vessel containing the sample and a separating reaction is allowed to take place. Then any other required steps are performed in other vessels, and finally the particles are moved to the measuring vessel. Mediums needed for the determination are dosed beforehand into the vessels.

The particles are preferably magnetic particles, whereby the remover preferably contains a magnet which can be moved in relation to the remover.

The vessels are preferably formed as one unit. In principle, however, some steps, especially measuring of the formed reaction product, can be performed outside the vessel unit, if desired. An outside measuring vessel could be used especially when the complex is detected directly from the solid phase, for example, fluorometrically or radiometrically.

Correspondingly, several steps, e.g. washes, can also be performed in the same vessel. A medium can also be dosed into some vessel or removed from it. Separate dosings could possibly be used in those steps where exact dosing is not necessary and where, for example, the same medium is used in several different determinations. Washes, in particular, could be such steps. However, normally such vessel units are more advantageous where all different mediums are ready in different vessels.

At least washes are usually performed in intermediate determination steps. In addition, the resulting reaction complex is usually joined in a middle step to a tracer which is then detected in the measuring step. The tracer can be either directly detectable or it can be a tracer which releases a detectable compound from a special substrate. Detection usually takes place fluorometrically, luminometrically, absorptiometrically or radiometically.

There is no risk of contamination in the method, because the sample is not drawn into the equipment from the plate vessels. In addition, the method can be carried out using simple and very reliably-operating automatic equipment.

The invention is suitable, for example, for immunologic, DNA-hybridization or hormone determinations.

The remover surface is preferably such that liquid will run off it as completely as possible. Preferably there is also a tip at the bottom end. The bottom of the reaction vessel is advantageously designed with the same shape as the remover, whereby as little medium as possible will be needed.

A very large solid-phase surface area is obtained by using solid-phase particles which are separate from the remover. The most advantageous ones are so-called microparticles. Magnetic particles are preferably used which are made to adhere easily to the remover with the aid of a magnet.

When using non-magnetic separate particles, the remover is provided, for example, with a grid or a filter to separate the particles from the medium.

To speed up mass transfer and thus also the necessary reaction time, the medium is preferably agitated during the reaction. This is preferably done by moving the remover. It is especially advantageous to move the remover in a vertical direction, whereby the medium must flow through a gap between the vessel and the remover, thus blending very effectively. To make blending more effective the remover is made so wide that a gap of a suitable narrowness is formed between the vessel and the remover. Agitation can also be promoted by a suitable remover and vessel design.

The vessel unit forms a plate for use in one determination. The remover can be packed into some vessel in the plate. The vessels for use in different steps may also be of different sizes.

The vessels are preferably closed with a film, which is punctured while carrying out the method. The film can be punctured by using the remover, but a separate puncturing point may also be used. The point may have cutting blades which form strips which tear in a controlled manner. The puncturing point may be attached to the same actuator as the remover in the equipment. The top edge of the vessel preferably has an extension against which the strips of the punctured film can rest. Closed vessels may contain an inert vapour phase to improve durability.

The equipment can also have a safeguarding system, which will make sure before the step is started that the vessel contains a medium. The remover may work conveniently as the indicator of such a system based on electric conductivity measurement.

If desired, in that reaction vessel in particular into which the sample is brought some suitable substance may be fastened to the vessel wall or to a separate solid phase remaining in the vessel, which substance binds such substances from the sample or from the formed complex which may disturb later determination steps.

The plate vessels are preferably in a single straight row, whereby the remover need be moved only along a straight path in the horizontal plane in relation to the plate. The vessels for the different steps may be located in any order in relation to each other. The vessels are preferably permanently fixed to one another. The plate may be made of some suitable material, preferably of plastic.

The plate is advantageously provided with detents and the equipment provided with their counterparts, so that the plate can not be located in a wrong position by mistake.

Figure 3:
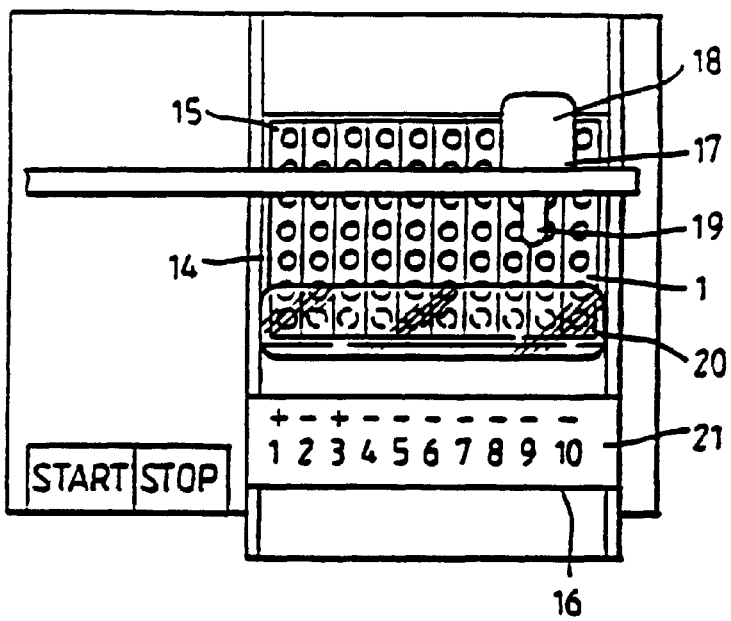
Figure 6:
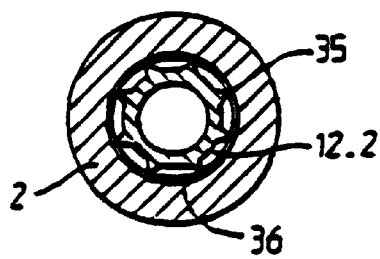
Figure 5:
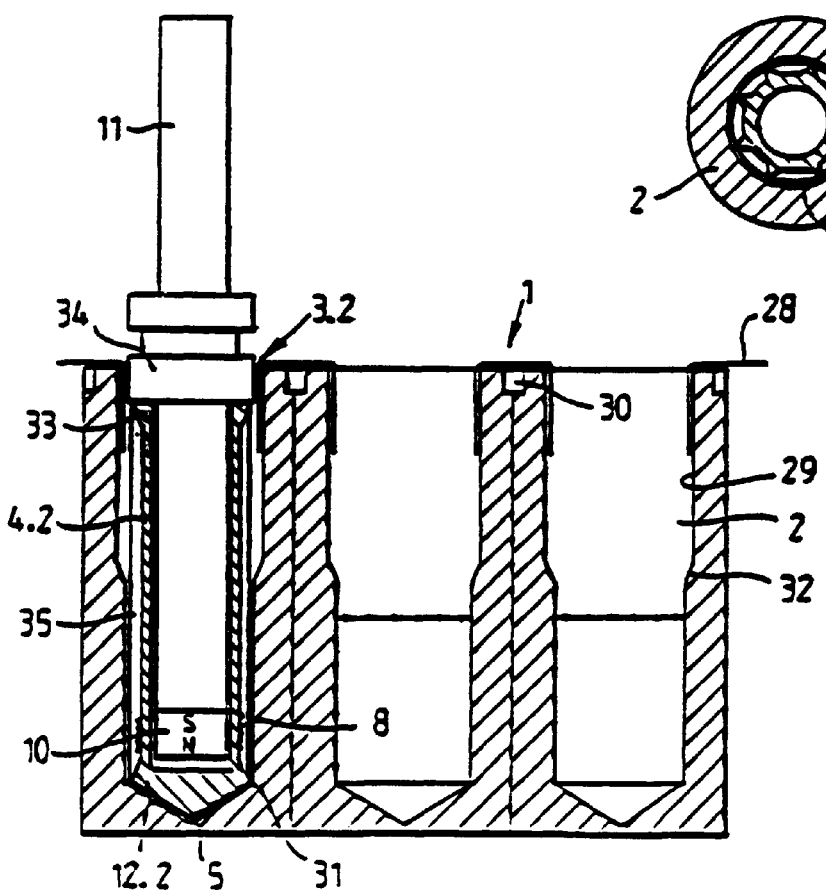
Figure 4A:
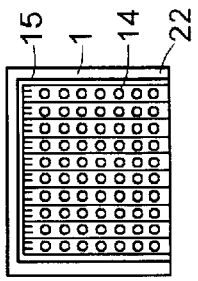
Figure 4:
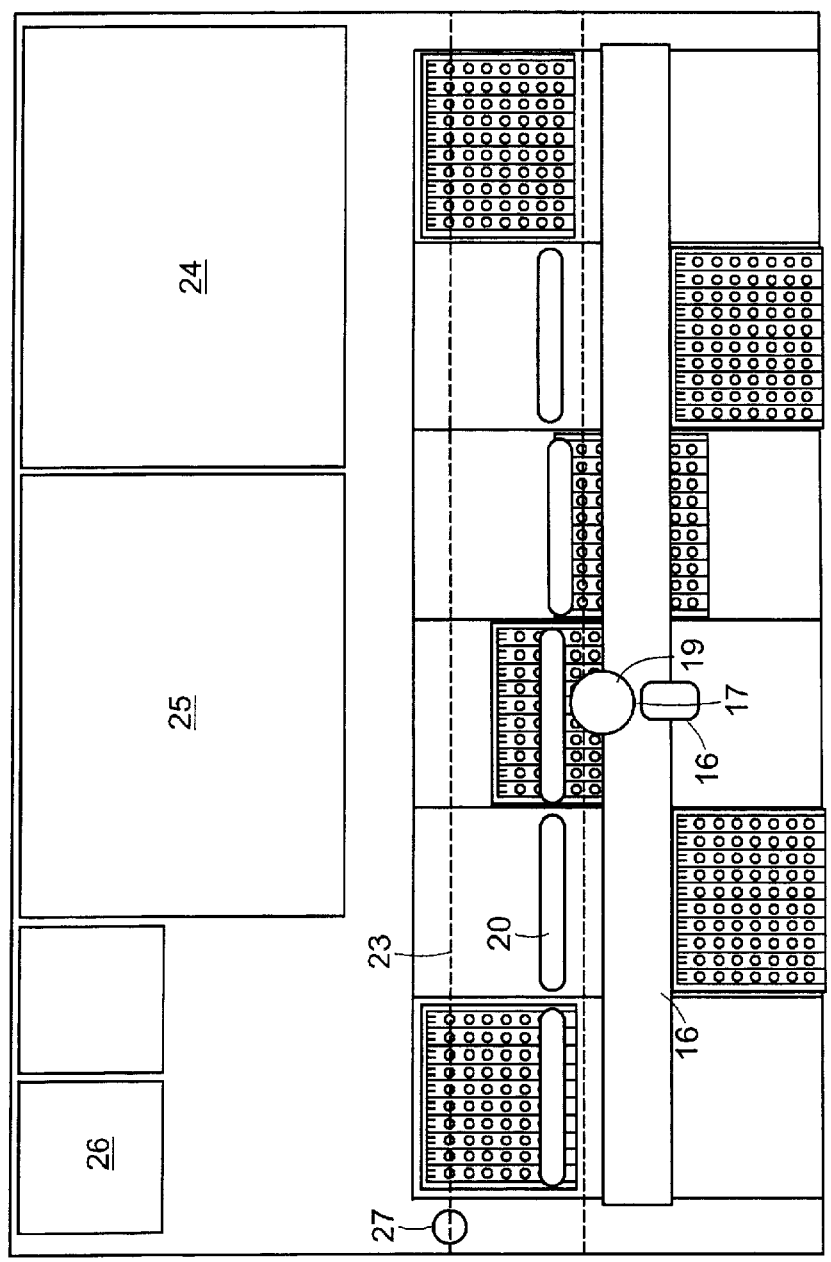

Some applications of the invention will be described in the following by way of example. In the drawings of the description FIG. 1 shows a magnetic particle remover in a reaction vessel for use in implementation of the method, FIGS. 2a and 2b show implementation of the method by using magnetic particles and another remover, FIG. 3 shows a set of equipment usable in implementation of the method, FIG. 4 shows another set of equipment of greater capacity, FIG. 5 shows a third magnetic particle remover located in a reaction vessel and usable for implementation of the method, and FIG. 6 shows a top view of the remover in FIG. 5.

In accordance with FIG. 1, immunodetermination is performed by using a plate 1, which consists of wells 2 located in a straight line and a remover 3 provided with a cylindrical sheath 4. At its bottom end the remover has a sharp point 5 and the bottom end is shaped as a cone 6. At its top end the remover has a handle 7 which is advantageous for robotics and at which the remover can be grasped for exact control of its horizontal and vertical positions. The well also contains magnetic particles 8 coated with a separating reagent which reacts to form a complex with the analyte to be determined. The remover has a bore 9 containing a movable pin 11 provided with a magnet 10.

The magnet 10 in FIG. 1 has two magnets one above the other so that identical poles are opposite to one another (SN-NS). In this way a powerful change of the magnetic field is created at the junction of the magnets and also an advantageous situation for pulling the particles to this point on the remover 3 surface. Correspondingly, the outside field of the magnet couple weakens in the vertical direction, whereby particles will gather more easily only at the location of the magnets. Several magnets can be placed similarly after each other. This is advantageous when a narrow structure is desired.

The sample to be examined is brought first to the first well 2 in plate 1 containing a suitable diluter, if required, whereupon magnetic particles 8 coated with the desired separating reagent and a remover 3 are brought into it. At this stage pin 11 is in the upper position, so the particles are moving freely in the well. The analyte possibly contained in the sample is now allowed to react with the separating reagent to form an immunocomplex. During the reaction the remover is moved in the well to promote blending. After incubation the magnet is moved to the lower position, whereby the particles will gather onto the remover surface and they can be moved to the second well. In the second well the particles can again be realeased, for example, to perform washing or a tracer reaction, and they can then be reassembled and then moved forward. Finally, the measurement required for the determination is performed in the last well.

During reactions and washes the remover 3 is moved back and forth in well 2, whereby the medium will blend effectively.

Plate 1 can be made of some suitable plastic material.

No liquid transfers are required during the determination, whereby a safe, simple and reliably-operating system can be constructed.

The cover 4 diameter is chosen to match the well 2 diameter so that an efficient flow is achieved around the cover when lifting or lowering the cover. When separating particles, several movements back and forth are preferably done with the cover in the well (for example, about 20 times in 10 seconds). Weakly adhered particles will then drop off, but then they will probably adhere better.

FIGS. 2a and 2b show implementation of the method by using a remover of another design.

The first well 2 in plate 1 contains magnetic microparticles 8 coated with a separating reagent for the analyte to be determined, and a diluter, if required.

Remover 3.1 has a boring 9 from the top which can receive pin 11 which has a magnet 10 at its lower end. At its lower end the remover has a drop-like extension 12 and its point has a sharp cusp 5. In addition, an annular recess 13 is provided in the extension surface close to its lower end.

The sample is brought to the first well 2, whereafter remover 3.1 is pushed into it with pin 11 in the upper position. When the remover is moved, the medium and particles 8 will blend effectively to form a suspension. Upon completion of the incubation the pin is pushed down, whereby the particles will gather onto the extension 12 surface pulled by magnet 10 and form a dense mass in recess 13 (see FIG. 2b). The remover is now moved to the next well and the pin is pulled up, whereby the particles will again blend with the medium. The particles are taken to the second well containing a first washing fluid, to the third well containing a second washing fluid and to the fourth well containing an enzyme conjugate adhering to the immunocomplex. After tracer incubation the remover is taken through three more reaction and washing wells for measurement in the last well containing an enzyme substrate, from which the enzyme removes a fluorometrically detectable compound. After the substrate reaction, the remover is moved aside and a fluorometric measurement is performed in such a way that both excitation radiation and emission radiation are led through the well mouth.

Light need not be led through the well wall in the determination. For this reason, as cheap a material and as simple a manufacturing technology as possible may be used. To reduce background radiation, the material is preferably opaque.

Luminometric determinations can be carried out in a similar manner.

If the reaction result is measured absorptiometrically, the measuring vessel must be transparent or the radiation must be obtained by a special arrangement (for example, a reflecting bottom) from the measuring vessel to the detector.

FIG. 3 shows a set of equipment where ten determinations may be performed at the same time.

Determination plates 1 are located in cassette 14. At the end of the last well in each plate there is a code 15 telling the equipment about the determination in question. In addition, the code may be used to give other data, especially the ageing time.

Cassette 14 is pushed into the equipment in the longitudinal direction of the plates with the code end first through opening 16, whereupon the cassette will be moved automatically. In the plate crosswise direction the equipment has a movable detector head 17 provided with an identifying dice 18 for reading the code and a measuring device 19 for establishing the reaction result. Removers and puncturing units for the well closing films, if such are used, and magnet pin moving units, if such are used, are all located on arm 20. The equipment also has a thermostatic heater for keeping the plates at the desired temperature.

A remover for each sample plate is attached to arm 20. Samples are dosed into the first well in plates 1 in cassette 14 and the cassette is pushed inside. It moves to its extreme position, where identifying device 18 reads code 15, whereby the control unit receives the information needed for performing the determination. The removers are lowered into the first wells. After incubation the removers are lifted up, the plate is moved one step forward and the second step is performed. The process goes on in this way from one well to the next and finally measurement is performed in the last well. The determination result for each plate is shown on display 21.

All determinations may be different provided that they can be performed in the number of wells available in the plate. All wells may not be needed in all determinations, in which case they do not contain any medium.

Such equipment can of course also be used where both the detector head and the removers are mounted on the same arm.

FIG. 4 shows a modular set of equipment where six cassettes can be handled at the same time.

In plates 1 used in this equipment code 15 is located at the end of the first well. Cassettes 14 are preheated in incubator 22 and they are pushed into the equipment with their code end first through feed opening 16. The removers needed for each cassette are located on arms 20 in the places for the corresponding plates.

The equipment has one common detector head 17, which can be moved in a transverse direction and which has an identifying device 18 and a measuring device 19. The identifying device reads code 15 in each plate and the cassette then moves inward to its extreme position, where a sample and possibly also a diluter is dosed into the first well. Dashed line 23 shows the path of movement of the dosing device. The cassette is then moved outward, so that the first well is located under remover arm 20, and the first step is performed. The cassette is then moved step by step inward, until the last wall is located at the measuring device.

FIG. 4 shows a schematic view of the power supplying unit 24, control unit 25, sample dosing pump 25, airing and diluter unit 26 and point washing well 27 in the equipment.

Plate 1 in FIG. 5 is closed by film 28, which is punctured by using remover 3.2. At the mouth of wells 2 there is an enlarged part 29 against which the punctured film will rest. In the top surface of the plate there is a gap 30 between the wells. It reveals any leakage points that may exist between the wells and it also prevents liquids from moving from one well to another through such points of leakage.

The boring in remover 3.2 contains a movable pin 11 with a magnet 10 at its lower end.

Remover 3.2 has an extension 12.2 at its lower end. Its lower part is conical with a sharp point 5. In this way, the extension can be used for puncturing film 28 so that magnetic particles 8 are protected in the sheath above the extension. The extension also functions as an efficient agitating piston. The bottom of wells 2 is shaped conically to match the extension.

Edge 31 in extension 12.2 is made sharp to minimize drop adhering. Correspondingly, lower edge 32 of the enlarged part of well 2 is suitably flared out downward to remove any remaining drop from remover 3.2 as this is removed from the well.

The upper end of remover 3.2 is provided with a conical mouth extension 33, which makes it easier to centralize the sheath in well 2. A plug 34 to close the well mouth is located above the mouth extension.

The remover 3.2 surface above extension 12.2 is provided with vertical ridges 35. Magnetic particles 8 are located in grooves 36 between these ridges and are thus protected during transfer. The groove bottoms are shaped suitably flat to facilitate release into the liquid. The protecting ridges may also be threadlike (for example, one thread with two ends).

What is claimed is:

1. An apparatus for separating magnetic particles from a fluid sample in a biological analysis, the apparatus comprising:
   a. a vessel for containing the magnetic particles and the fluid sample wherein the vessel has a lower portion with a smaller diameter and an upper portion with a larger diameter, and an edge between the upper portion and the lower portion;
   b. a magnetic remover for collecting the particles from the vessel; and
   c. a positioner constructed to position the magnetic remover into the vessel such that particles are adhered thereto and remove the magnetic remover from the vessel such that said particles adhered thereto are removed from the vessel.

2. The apparatus of claim 1, wherein the edge flares upwardly outward.

3. The apparatus of claim 1, wherein the magnetic remover has a body, the lower end extends to a smaller diameter and the magnetic remover has a sharp transition between the body and the lower end.

4. The apparatus of claim 1, wherein the magnetic remover has a sharp point at the lower end.

5. The apparatus of claim 4 wherein the vessel includes a puncturable film at a top end.

6. The apparatus of any one of claims 1–3, wherein the upper portion and the lower portion are substantially cylindrical.

7. An apparatus for separating magnetic particles from a fluid sample in a biological analysis, the apparatus comprising:

a. a vessel for containing the magnetic particles and the fluid sample wherein the vessel has a lower portion with a substantially constant cross-sectional width and an upper portion with a substantially constant cross-sectional width and wherein the width of the upper portion is greater than the width of the lower portion;

b. a magnetic remover for collecting the particles from the vessel; and c. a positioner constructed to position the magnetic remover into the vessel such that particles are adhered thereto and remove the magnetic remover from the vessel such that said particles adhered thereto are removed from the vessel.

8. The apparatus of claim 7, wherein vessel has an edge between the upper portion and the lower portion and wherein the lower edge flares upwardly outward.

9. The apparatus of claim 7, wherein the magnetic remover has a sharp point at the lower end.

10. The apparatus of claim 7, wherein the magnetic remover has a body and a lower end extending to a smaller diameter and the magnetic remover has a sharp transition between the body and the lower end.

11. The apparatus of claim 10, wherein the vessel includes a puncturable film at a top end.

* * * * *